(12) United States Patent
Guilleuma

(10) Patent No.: US 12,201,438 B2
(45) Date of Patent: Jan. 21, 2025

(54) METHOD FOR DIAGNOSING AND TREATING HEMORRHOIDS

(71) Applicant: Juan Guilleuma, Madrid (ES)

(72) Inventor: Juan Guilleuma, Madrid (ES)

(*) Notice: Subject to any disclaimer, the term of this patent is extended or adjusted under 35 U.S.C. 154(b) by 877 days.

(21) Appl. No.: 15/957,103

(22) Filed: Apr. 19, 2018

(65) Prior Publication Data

US 2018/0303402 A1 Oct. 25, 2018

Related U.S. Application Data

(60) Provisional application No. 62/487,136, filed on Apr. 19, 2017.

(51) Int. Cl.
*A61B 5/00* (2006.01)
*A61B 5/055* (2006.01)
(Continued)

(52) U.S. Cl.
CPC ............ *A61B 5/4255* (2013.01); *A61B 5/004* (2013.01); *A61B 5/1076* (2013.01); *A61B 5/4842* (2013.01); *A61B 6/504* (2013.01); *A61B 8/0891* (2013.01); *A61F 2/82* (2013.01); *A61F 2/958* (2013.01); *A61M 25/104* (2013.01);
(Continued)

(58) Field of Classification Search
CPC ..... A61B 5/4255; A61B 6/032; A61B 5/1076; A61B 5/004; A61B 8/0891; A61B 6/504; A61B 5/4842; A61B 2017/00818; A61B 5/055; A61B 8/488; A61B 8/12; A61B 5/0066; A61B 5/4836; A61B 17/22;
(Continued)

(56) References Cited

U.S. PATENT DOCUMENTS 6,135,997 A 10/2000 Laufer et al.
8,257,265 B1* 9/2012 Raju ................. A61B 8/12
600/462
(Continued)

OTHER PUBLICATIONS

JM Holdstock et al., "Heamorrhoids are associated with internal iliac vein reflux in up to one-third of women presenting with varicose veins associated with pelvic vein reflux", 2015, Phlebology, vol. 30, pp. 133-139 (Year: 2015).*
(Continued)

*Primary Examiner* — Patricia J Park
*Assistant Examiner* — Adil Partap S Virk
(74) *Attorney, Agent, or Firm* — St. Onge Steward Johnston & Reens LLC; Stephen P. McNamara

(57) ABSTRACT

A method of determination of a cause of hemorrhoids in a subject includes a determination of the presence of hemorrhoids in the subject by visual inspection, and by one or more of a non-invasive medical imaging procedure and/or an intra-vascular visualization procedure, determining if there is an obstruction or occlusion in an iliac vein of the subject, and if so, determining that the hemorrhoids were caused by such obstruction or occlusion. If the obstruction or occlusion are determined to be the cause of the hemorrhoids, a procedure for compressing the obstruction or occlusion in the iliac vein of the subject, such as by angioplasty or stenting, is performed. After an appropriate time period, changes to the hemorrhoids in the subject are determined by a subsequent visual inspection.

6 Claims, 5 Drawing Sheets

(51) Int. Cl.
*A61B 5/107* (2006.01)
*A61B 6/03* (2006.01)
*A61B 6/50* (2024.01)
*A61B 8/08* (2006.01)
*A61B 8/12* (2006.01)
*A61B 17/00* (2006.01)
*A61B 17/22* (2006.01)
*A61F 2/82* (2013.01)
*A61F 2/958* (2013.01)
*A61M 25/10* (2013.01)

(52) U.S. Cl.
CPC ............ *A61B 5/0066* (2013.01); *A61B 5/055* (2013.01); *A61B 5/4836* (2013.01); *A61B 6/032* (2013.01); *A61B 8/12* (2013.01); *A61B 8/488* (2013.01); *A61B 2017/00818* (2013.01); *A61B 17/22* (2013.01); *A61B 2017/22001* (2013.01)

(58) Field of Classification Search
CPC .. A61B 2017/22001; A61F 2/82; A61F 2/958; A61M 25/104
See application file for complete search history.

(56) References Cited

U.S. PATENT DOCUMENTS

| | | | |
|---|---|---|---|
| 9,232,947 B2 | 1/2016 | Brenner et al. | |
| 2009/0248034 A1 | 10/2009 | Dolan et al. | |
| 2013/0211489 A1 | 8/2013 | Makower et al. | |
| 2014/0200568 A1* | 7/2014 | Sharma | A61B 5/1076 606/27 |
| 2014/0277365 A1 | 9/2014 | Gillespie | |

OTHER PUBLICATIONS

Javier Monedero et al. "Pelvic Congestion Syndrome: an update", 2013, Phlebolymphology, vol. 20 No. 3, pp. 145-149 (Year: 2013).*
Shahab Abdessalam et al., "Reoperation for Recurrent Anal and Perianal Conditions", 2008, Preoperative Pediatric Surgery, pp. 327-335 (Year: 2008).*
Katelyn Brinegar et al., "Iliac Vein Compression Syndrome: Clinical, Imaging, and Pathologic Findings", Nov. 28, 2015, World Journal of Radiology, vol. 7, Issue 11, pp. 375-381 (Year: 2015).*
Marlene O'Brien et al. "Diagnosis and Treatment of the Pelvic Congestion Syndrome", Jan. 2015, Journal of Vascular Surgery Venous and Lymphatic Disorders, pp. 96-106 (Year: 2015).*
Elizabeth Ignacio et al., "Pelvic Congestion Syndrome: Diagnosis and Treatment", 2008, Seminars in Interventional Radiology, vol. 25 No. 4, pp. 361-368 (Year: 2008).*
Shigeaki Umeoka et al., "Vascular Dilatation in the Pelvis: Identification with CT and MR Imaging", Jan.-Feb. 2004, RadioGraphics, vol. 24 No. 1, pp. 193-208 (Year: 2004).*
Leonardo Cavalcante et al., "Iliac Vein Compression Syndrome: Literature Review", Jan.-Mar. 2015, pp. 78-83 (Year: 2015).*
Hirsch, "What's the Difference Between a Treatment and a Cure?", 2017 (Year: 2017).*
The Editors of Encyclopedia Britannica, "Scientific Method", Aug. 22, 2014 (Year: 2014).*
O'sullivan, Gerard J., et al. "Endovascular management of iliac vein compression (May-Thurner) syndrome." Journal of Vascular and Interventional Radiology 11.7 (2000): 823-836.
Firas F. Mussa, et al.; "Iliac Vein Stenting for Chronic Venous Insufficiency"; Tex Heart Inst J. 2007; 34(1): 6-66.

* cited by examiner

METHOD FOR DIAGNOSING AND TREATING HEMORRHOIDS

FIELD OF THE INVENTION

The present invention relates to methods of diagnosing the cause of hemorrhoids in a subject, and treating hemorrhoids and preventing the recurrence of hemorrhoids.

BACKGROUND OF THE INVENTION

Hemorrhoids are a very common anorectal condition defined as the enlargement and distal displacement of the normal hemorrhoidal venous plexi. More specifically, hemorrhoids are swollen veins in the lower rectum and anus, similar to varicose veins. Hemorrhoids located inside the rectum are referred to as internal hemorrhoids, and those under the skin around the anus are referred to as external hemorrhoids. Swollen hemorrhoids have also been called piles.

It has been proposed that an increase in pressure in small blood vessels can cause hemorrhoids. Increased pressures can cause the small blood vessels to swell and engorge with blood. Such increased pressures have been attributed to a number of different factors, including: low fiber diet that causes a person to strain when having a bowel movement, increasing the pressure within the blood vessels; pregnancy and possible increased pressure of a uterus on the rectum and anus; poor posture; prolonged sitting on the toilet which may increase pressure within the hemorrhoid blood vessels; obesity; colon cancer; and other factors.

Internal hemorrhoids can become inflamed and swollen. The passage of stool may damage the hemorrhoid causing bleeding and muscle spasms and pain if they protrude or prolapse through the anus. Internal hemorrhoids can also clot causing significant pain. Inflamed hemorrhoids may leak mucus that can cause inflammation of the skin surrounding the anus causing burning and itching, known as pruritis ani.

External hemorrhoids are more protected by external layers of skin but can also cause pain when a clot forms, as when an underlying vein within the hemorrhoid clots causing intense pain from the rapid stretching of the skin covering the hemorrhoid. External hemorrhoids can also cause difficulties with cleaning after a bowel movement, leading to irritation and secondary skin infections.

The various degrees of hemorrhoid disease are classified by grade. Internal hemorrhoids are graded by the degree of prolapse below the pectinate line into the anal canal as defined below:

Grade 1: the internal hemorrhoid bulges into the canal but does not prolapse or fall completely into it.

Grade 2: the hemorrhoid protrudes past the anal verge with straining for a bowel movement or passage of flatus, but spontaneously return to their original internal position once the straining has subsided.

Grade 3: the hemorrhoid may protrude past the anal verge without any straining and requires the patient to push them inside manually.

Grade 4: the internal hemorrhoid always stays protruded or prolapsed and is at risk for thrombosis or strangulation should the anal muscles go into spasm.

Grade 1 hemorrhoids are treated conservatively with dietary changes (including increasing fiber and water intake) and medications. Grade 2 hemorrhoids that do not resolve with the above therapies are treated by a variety of methods, including sclerotherapy, rubber-band ligation, and infrared coagulation. Sclerotherapy is an injection therapy using a different sclerosing agents, which are injected into the hemorrhoid. The agent triggers an inflammatory response and as the blood flow into the hemorrhoid is interrupted, secondary fibrosis is facilitated, shrinking the hemorrhoid. Rubber band ligation is the most common and effective treatment. This method is fast and relatively pain-free, but has a recurrence rate of about 70% after 3 years and it usually requires several return visits to the physician. Infrared coagulation works by transforming infrared radiation to heat, which generates sclerosis and fixation of hemorrhoids.

Grade 3 hemorrhoids are candidates for several different surgical treatments, with a current emphasis on stapled hemorrhoidopexy, hemorrhoidectomy, and doppler-guided hemorrhoidal artery ligation (DHAL) (ligation of the distal branches of the superior rectal artery, resulting in a reduction of blood flow and decongestion of hemorrhoidal plexus). The efficacies of these therapies are approximately 80% for stapled hemorrhoidopexy and 70% for DHAL. Grade 4 hemorrhoids are typically treated by a surgical hemorrhoidectomy, which has an efficacy of 95% and almost no recurrence, but it causes a significant amount of postoperative pain, causing patients to miss work, and can risk complications such as permanent fecal incontinence.

Estimates of the prevalence of symptomatic hemorrhoidal disease in the United States of America (USA), range from 10 million people (prevalence rate 4.4%), from published data at Medscape General Surgery, to a National Center for Health Statistics report of up to 23 million (prevalence rate 12.8% of USA adults. In 2004, the National Institute of Health reported that the diagnosis of hemorrhoids was associated with 3.2 million ambulatory care visits, 306,000 hospitalizations and 2 million prescriptions in the USA. It has been stated that 50% of the population will experience symptomatic hemorrhoid disease at some point in their lives.

A diagnosis of hemorrhoids has typically been obtained by a direct examination of the hemorrhoids. Diagnosis is made by direct visualization of the hemorrhoids at the anus and anal canal; and in case of bleeding, excluding by endoscopic techniques other anatomic sources of the gastrointestinal tract.

As discussed above, the treatment of more severe grades of hemorrhoids involves a variety of surgical methods that have increasing risk of both immediate and long-term negative side effects. More importantly, the known surgical methods for treatment of hemorrhoids, while relieving the immediate problem of a particular hemorrhoid or group of hemorrhoids, does not address the underlying causes of the hemorrhoid or group of hemorrhoids and thus does not serve to prevent recurrence of the problem.

Therefore, there is a need for a cost-effective and novel method of treatment of every grade of hemorrhoids which minimizes pain and discomfort to a subject, and further prevents or reduces the likelihood of a recurrence of hemorrhoids.

SUMMARY OF THE INVENTION

A method of determination of a cause of hemorrhoids in a subject includes a determination of the presence of hemorrhoids in the subject by visual inspection, and the use of one or more of a non-invasive medical imaging system and/or an Intra Vascular Ultrasound (IVUS) system to determine if there is an obstruction or occlusion in an iliac vein of the subject, and if so, determining that the hemorrhoids were caused by such obstruction or occlusion.

A method of prevention and/or treatment of hemorrhoids is based on a determination that an obstruction or occlusion in an iliac vein of the subject is the cause of hemorrhoids, and in such circumstances a procedure for increasing a cross-sectional area of a lumen of the obstructed or occluded portion of the iliac vein of the subject, such as by angioplasty or stenting, is performed. After an appropriate time period, changes to the hemorrhoids in the subject are determined by a subsequent visual inspection.

The methods of the invention have been effective in clinical studies in the determination of a cause of hemorrhoids, treating hemorrhoids, and preventing their reoccurrence.

DETAILED DESCRIPTION OF THE INVENTION

Figure 1:
FIG. 1 is a photograph of the interior of an iliac vein showing a stenotic or compressed (obstructed or occluded) portion of an iliac vein as visualized using an Intra Vascular Ultrasound (IVUS) system.

The present invention derives from an effort to determine the cause of hemorrhoids, and to develop a method to prevent and treat the cause of hemorrhoids, rather than only treating the symptoms.

The pelvic venous system includes group of veins which drain the anal channel to an internal iliac vein, which then connects to a common iliac vein. The pelvic venous system includes a femoral vein, an internal iliac vein, an external iliac vein, and a common iliac vein which begins where the internal iliac vein and external iliac vein join together. The pelvic venous system includes inferior and middle hemorrhoidal plexi which drain to the iliac veins. The superior hemorrhoidal plexus drains to the portal system. Blood flow inside the hemorrhoidal vein plexus is unidirectional from the superior hemorrhoidal group to the inferior hemorrhoidal group.

The present invention is based in part on the recognition that obstruction of the internal iliac vein and/or common iliac vein may increase local venous pressure in the area of the lower rectum and anus, causing hemorrhoids. The present invention recognizes that vein stenosis, the progressive narrowing of a vein, and compression, will cause venous hypertension which in turn cause hemorrhoid development and progression.

Vein stenosis and/or chronic obstructive and occlusive lesions can arise from a variety of causes including trauma, pressure, and buildup of deposits on the inner walls of the vein.

Vein compression may be caused by physiological structures or by external factors. A common example of vein compression is May-Thurner syndrome. The syndrome is caused by an anatomical variant in which the right common iliac artery overlies and compresses the left common iliac vein against the lumbar spine. The compression or pinching of the left common iliac vein outflow can lead to iliofemoral deep venous thrombosis (DVT), edema, and pain.

The present invention is accordingly directed at a method of determination of the cause of hemorrhoids in a subject by detection of vein stenosis and/or compression, and the subsequent prevention and treatment of hemorrhoids by the reduction of vein stenosis and/or compression. In particular, such methods are directed at detection and reduction of iliac vein stenosis and/or compression.

A method of determination of a cause of hemorrhoids in a subject comprises steps of: visual inspection of a lower rectum and anus of a subject to determine the presence of hemorrhoids in a subject; performing one or more of: (i) a non-invasive medical imaging procedure and (ii) an intra-vascular visualization procedure; to determine if there is a stenosis or compression of an iliac vein of the subject; and determining that a cause of the hemorrhoids in the subject are the stenosis or compression of an iliac vein in the subject if the subject is determined to have hemorrhoids and a stenosis or compression of the iliac vein. Preferably, the iliac vein is a common iliac vein. In some embodiments, the iliac vein is an internal iliac vein.

In some embodiments, the non-invasive medical imaging is performed by one or more of a computed tomography pelvic scan system, a pelvic magnetic resonance imaging system, a computed tomography angiography system, a magnetic resonance angiography system, a computed tomographic venography system, a magnetic resonance venography system, a duplex scan venography system, an ultrasonography system, or an iliocavography system. Preferably, the non-invasive medical imaging system is a color Doppler ultrasonography system.

In preferred embodiments, the intra-vascular visualization procedure is conducted using an Intra Vascular Ultrasound (IVUS) system and/or an optical coherence tomography angiography (OCT-A) system.

In some embodiments it may be sufficient to conduct only non-invasive medical imaging to determine if there is a stenosis or compression of an iliac vein of the subject. In other embodiments, the non-invasive medical imaging is not sufficient and an intra-vascular visualization procedure is also necessary. In other embodiments, non-invasive medical imaging may be omitted and intra-vascular visualization procedures initiated either pre-operatively or in conjunction with procedures to reduce stenosis or compression of the iliac vein.

If the subject is determined to have hemorrhoids and an obstruction or occlusion of the iliac vein, then it will be presumed that the hemorrhoids in the subject are caused by the obstruction or occlusion of the iliac vein in the subject. In such case, if it is desired to treat or prevent hemorrhoids then steps will be taken to reduce the stenosis or compression of the iliac vein (obstruction or occlusion of the iliac vein). The obstruction or occlusion can be reduced by applying intra-vascular pressure on the stenosis or compressed area of the iliac vein or the obstruction or occlusion. Such pressure will increase the cross-sectional area of the lumen of the obstructed or occluded portion of the iliac vein. Intra-vascular pressure can be applied to the obstruction or occlusion by one or more of angioplasty, balloon angioplasty, and stenting of the iliac vein. Preferably, intra-vascular pressure can be applied to the obstruction or occlusion by implantation of a self-expanding metallic stent or a balloon-expanded metallic stent in a stenosed or a compressed portion of the iliac vein of the subject.

After these procedures are complete, one or more subsequent visual inspections of the lower rectum and anus of the subject are conducted to determine changes to the hemorrhoids in the subject. Preferably such visual inspections are conducted at approximately 1, 3, 6, and 12 postoperative months.

The disclosures of U.S. Pat. No. 8,257,265, Pub. No. US 2014/0277365 and Pub. No. US 2009/0248034 are hereby incorporated by reference as additional background reference material on IVUS procedures and stent implantation procedures.

Methods according to the present invention involving venous IVUS and stent implantation are reasonably well developed and can be conducted using commercially available medical equipment. The procedures will typically require (1) expandable products—such as a sheath, guide wire and catheter; (2) a stent; (3) a balloon; and (4) and IVUS probe (for diagnosis). The cost of procedures using such equipment would not be expected to be unusual or challenging. Thus the present invention provides a cost-effective approach to treatment and prevention of hemorrhoids.

Clinical studies were conducted on patients with hemorrhoids to determine the efficacy of the methods of the invention. The studies are described in the following examples.

EXAMPLE 1

A Clinical Study Performed on 20 Patients with Hemorrhoids

Twenty (20) human subjects with hemorrhoids were selected for the study. Appropriate disclosures regarding the study were made and consents were obtained. Visual inspection of each subject was made to confirm the presence of hemorrhoids. Each subject was further examined by performing iliocavography to determine if there was a stenosis in or a compression of an iliac vein of the subject. Iliac vein study was conducted by Intra Vascular Ultrasound (IVUS) visualization of the common and external iliac veins. In each case, common iliac vein lumen stenosis or extrinsic vein compression (IVSEC) was found. In accordance with the recognition that obstruction or occlusion of the iliac veins may increase local venous pressure in the area of the lower rectum and anus, thereby causing hemorrhoids, a self-expanding metallic stent (Wallstent™, manufactured by Boston Scientific, Minneapolis, Minn) was implanted in the stenosed or compressed portion of the iliac veins of the subject. Balloon angioplasty was performed when necessary to further open up the iliac vein lumen (XXL Esophageal, Boston Scientific, Minneapolis, Minn). A further IVUS visualization of the iliac vein was completed to verify the implant. The stent sheaths were retrieved and a final step of direct smooth compression was performed.

The subjects were interviewed 24 hours after the procedure and they reported improvements in symptoms of pain and itching. In subsequent follow up examinations hemorrhoid bleeding and prolapsing were significantly improved or eliminated within 6-12 months of the procedure. The subjects did not have a recurrence of hemorrhoid symptoms even after 12 months or more.

It was determined based on the results of the study of Example 1 that the inventive hypothesis that obstruction or occlusion of the iliac veins may increase local venous pressure in the area of the lower rectum and anus, thereby causing hemorrhoids, was a correct hypothesis. Further, the long term results of the study of Example 1 established that the methods used in the study provided a method of treatment and prevention of hemorrhoids.

EXAMPLE 2

A Clinical Study Performed on 5 Patients with Grade>1 Hemorrhoids

Five (5) human subjects with hemorrhoids were selected for the study. Appropriate disclosures regarding the study were made and consents were obtained. Visual inspection of each subject was made to confirm the presence of hemorrhoids. Each subject was further examined by non-invasive medical imaging systems, specifically, color Doppler ultrasonography of the lower extremities and pelvis to identify any obstructive lesions. Computed tomographic venography or magnetic resonance venography was performed in all subjects in an attempt to identify compressive iliac vein pathology, for instance a May-Thurner syndrome. No preoperative iliocavography was performed.

The subjects were provided with local anesthesia and sedation. The following procedures were performed in an operating room. The iliac veins of the subject were accessed via the femoral vein, which connects to the external iliac vein and then to the common iliac vein. The Seldinger technique, using 11F sheaths, was used. After catheterization of the lesion, bilateral iliocavography was performed. Iliac vein study was conducted by Intra Vascular Ultrasound (IVUS) visualization of the common and external iliac veins using an IVUS probe (Atlantis™ SR Pro Imaging Catheter, Boston Scientific, Minneapolis, Minn). The probe was connected to an iLab™ Ultrasound Imaging System (Boston Scientific, Minneapolis, Minn). The probe was inserted into the common femoral vein and advanced into the iliac venous systems. The iliac venous systems and their pathways were examined. All of the subjects were found to have bilateral iliac venous system obstructions and occlusions.

Figure 2:
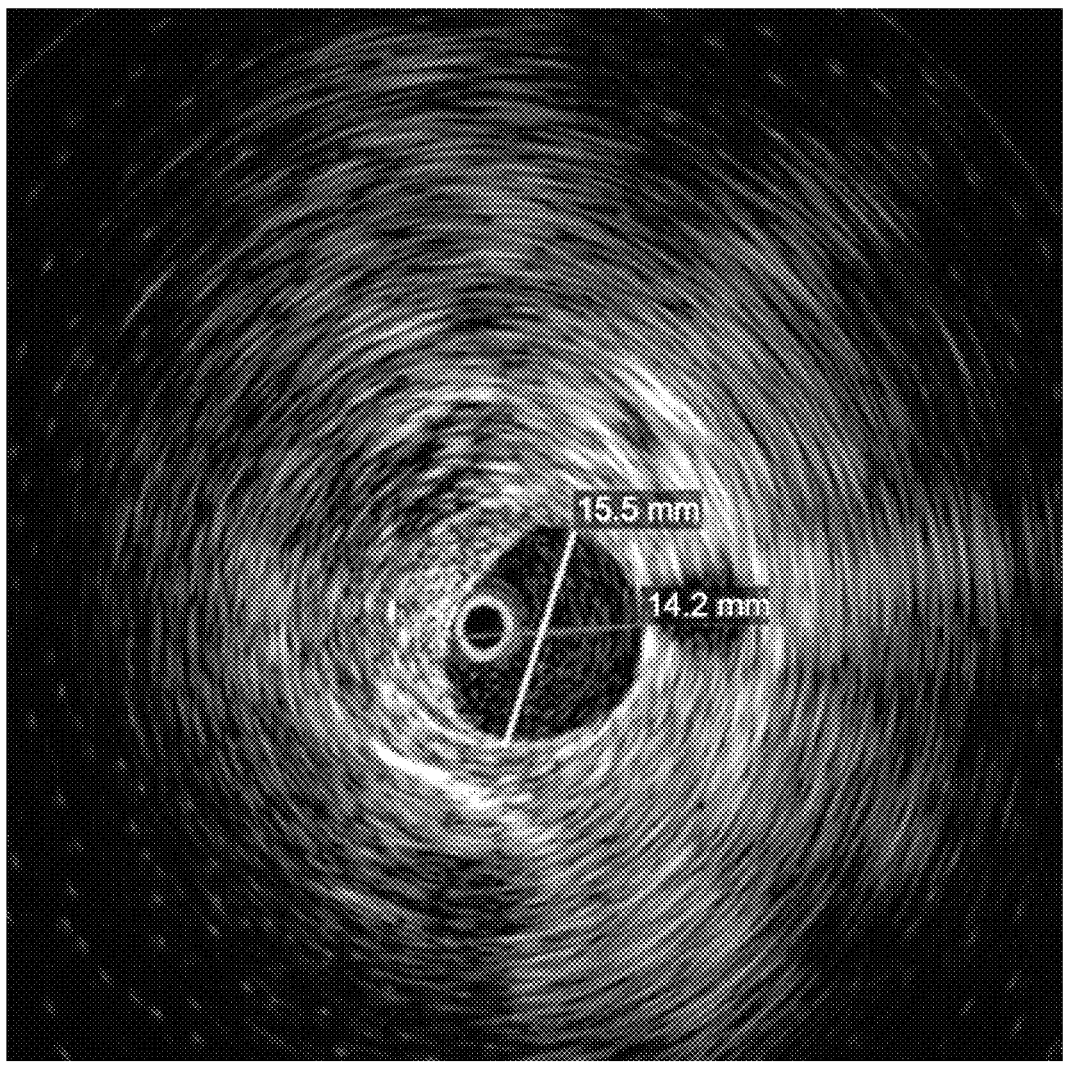
FIG. 2 is a photograph of the interior of an iliac vein showing a normal portion of an iliac vein as visualized using an Intra Vascular Ultrasound (IVUS) system.

FIG. 1 is a photograph of the interior of an iliac vein showing a stenotic or compressed (obstructed or occluded) portion of an iliac vein as visualized using the Intra Vascular Ultrasound (IVUS) system. In FIG. 1, the vein lumen is a flattened shape having a reduced cross-sectional area, and thus reducing flow therethrough and increasing pressure in blood vessels in the portions of the vessels before the stenotic or compressed (obstructed or occluded) portion of an iliac vein. In contrast, FIG. 2 is a photograph of the interior of an iliac vein showing a normal portion of an iliac vein. In FIG. 2, the vein lumen is an oblong shape having a greater cross-sectional area that the area shown in FIG. 1, and thus has a greater flow therethrough and does not cause pressure buildup in blood vessels in the portions of the vessels before the photographed area.

A self-expanding metallic stent (Wallstent™, manufactured by Boston Scientific, Minneapolis, Minn) was implanted in the obstructed and occluded portions of the iliac veins of the subjects. Balloon angioplasty was performed when necessary to further open up the iliac vein lumen (XXL Esophageal, Boston Scientific, Minneapolis, Minn). A further IVUS visualization of the iliac vein was completed to verify the implant. The stent sheaths were retrieved and a final step of direct smooth compression was performed.

In the five subjects, 10 venous segments were treated, all in the common iliac veins. The technical success rate was 100%. Eleven stents (18-22 mm in diameter and 40-90 mm long) were used all in the common iliac veins. In all cases, the stent proximal end was deployed beyond the iliocaval junction, and one common iliac vein was treated with two stents. The mean number of stents per patient was 2.2 (2-3). The mean length of stented vein segments was 58 mm (range 40-120 mm). No concomitant procedures were performed and no patients had early or midterm thrombosis.

Figure 3:
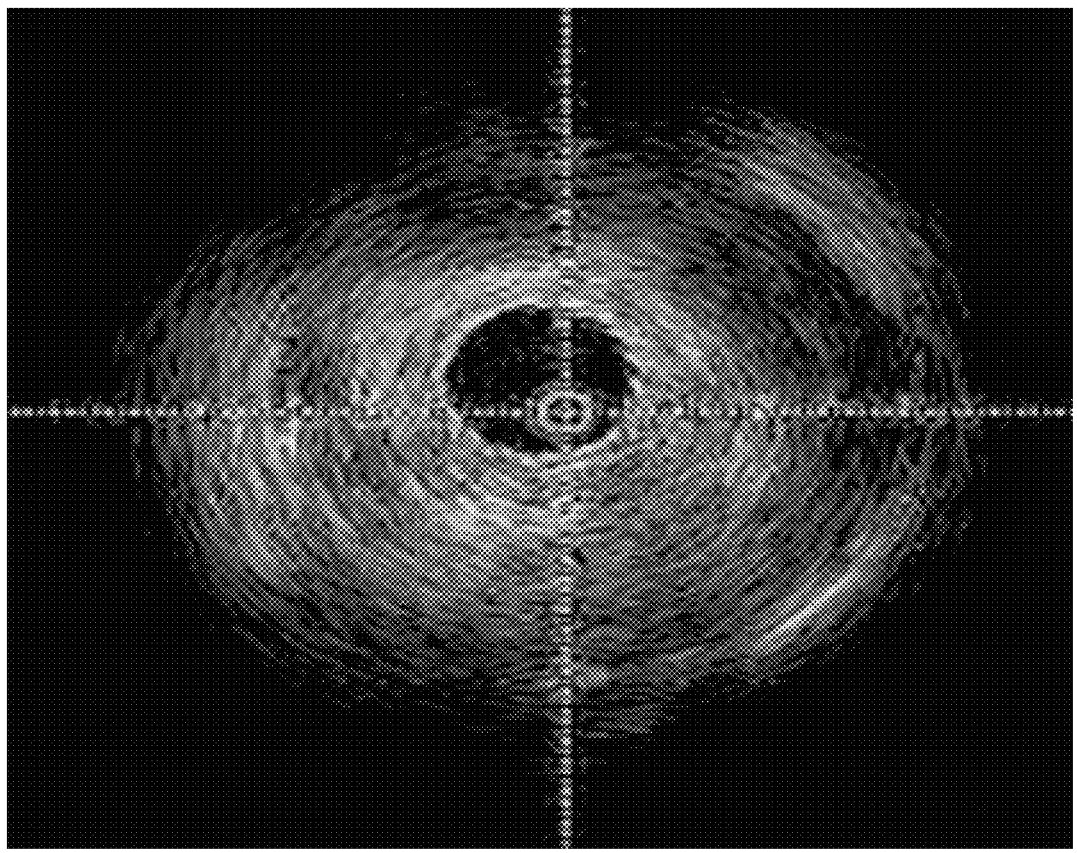
FIG. 3 is a photograph of the interior of an iliac vein showing a stenotic or compressed (obstructed or occluded) portion of an iliac vein after implant of a self-expanding metallic stent as visualized using an Intra Vascular Ultrasound (IVUS) system.
Figure 4:
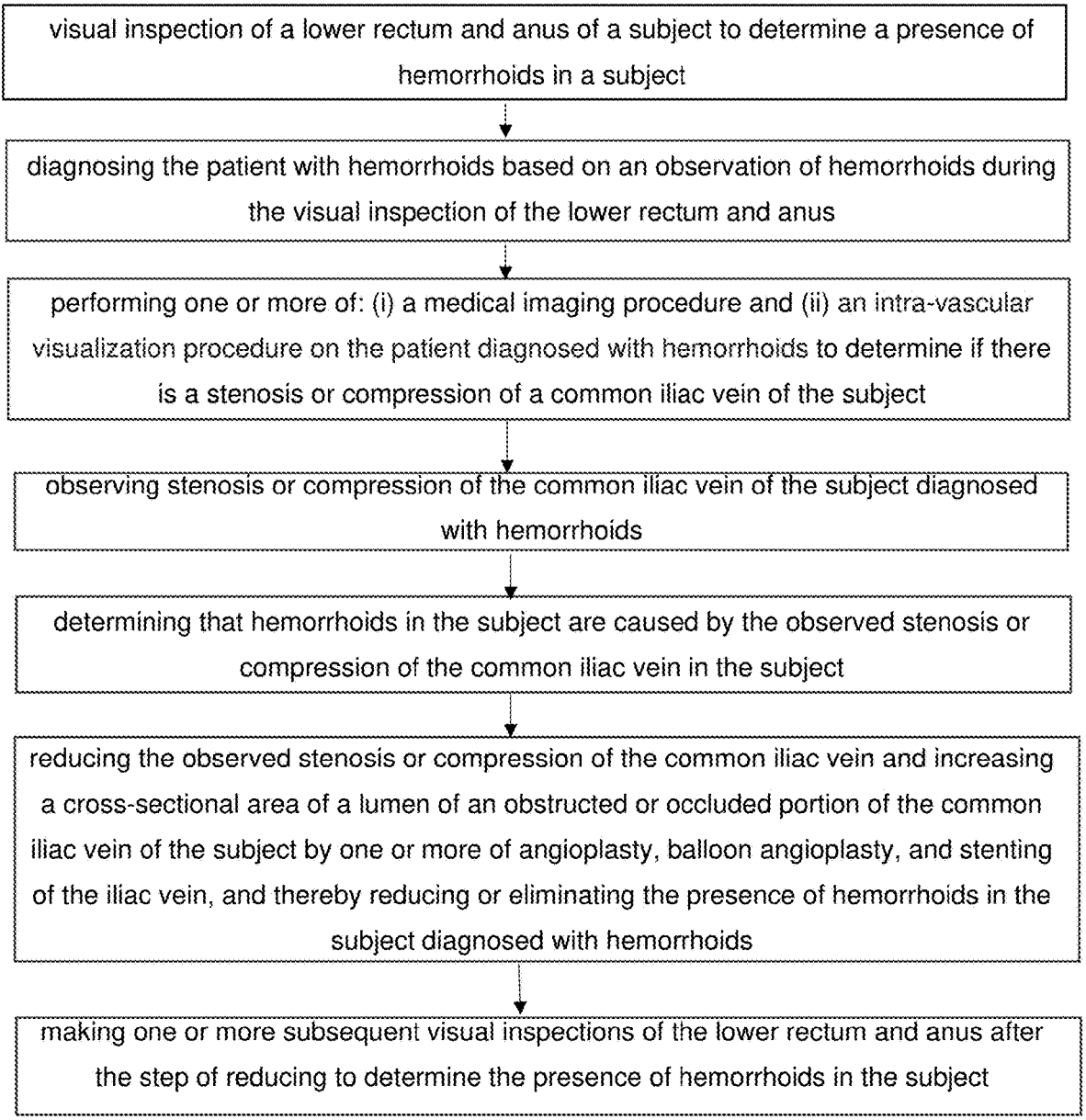
FIG. 4 is a block diagram illustrating the steps of the invention.
Figure 5:
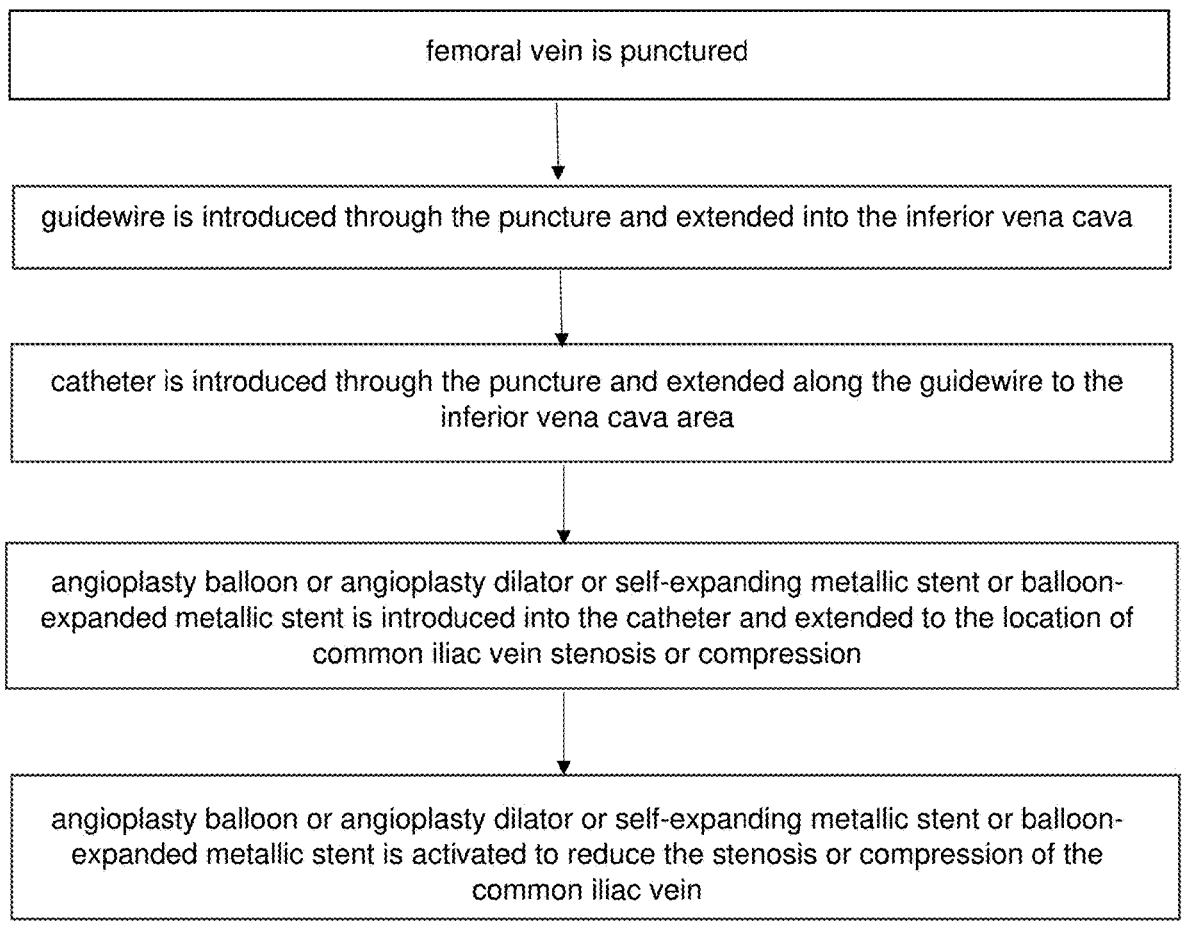
FIG. 5 is a block diagram illustrating the steps of implantation of a self-expanding stent, angioplasty, or balloon-expanded stent.

FIG. 3 is a photograph of the interior of an iliac vein showing a stenotic or compressed (obstructed or occluded) portion of an iliac vein after implant of a self-expanding metallic stent. In FIG. 3, the vein lumen is a circular shape having a greater cross-sectional area that the area shown in FIG. 1, and thus has a greater flow therethrough and does not cause pressure buildup in blood vessels in the portions of the vessels before the photographed area.

The results with the subjects of Example 2 were the same as the subjects of Example 1. The subjects reported improvements in symptoms of pain and itching after 24 hours of the procedures. Hemorrhoid bleeding and prolapsing were significantly improved or eliminated within 6-12 months of the procedure. The subjects did not have a recurrence of hemorrhoid symptoms even after 12 months or more.

The results of the study of Example 2 further confirm the inventive hypothesis that obstruction or occlusion of the iliac veins will lead to hemorrhoids. The results of the study of Example 2 confirm that the methods used in the study provide an effective method of treatment and prevention of hemorrhoids.

Having described the invention with reference to particular embodiments, theories of effectiveness, and the like, it will be apparent to those of skill in the art that it is not intended that the invention be limited by such illustrative embodiments or mechanisms, and that modifications can be made without departing from the scope or spirit of the invention.

What is claimed is:

1. A method of treatment of hemorrhoids in a subject, the method comprising the steps of:
    visual inspection of a lower rectum and anus of a subject to determine a presence of hemorrhoids in a subject;
    diagnosing the patient with hemorrhoids based on an observation of hemorrhoids during the visual inspection of the lower rectum and anus;
    performing one or more of: (i) a medical imaging procedure and (ii) an intra-vascular visualization procedure on the patient diagnosed with hemorrhoids to determine if there is a stenosis or compression of a common iliac vein of the subject;
    observing stenosis or compression of the common iliac vein of the subject diagnosed with hemorrhoids;
    determining that hemorrhoids in the subject are caused by the observed stenosis or compression of the common iliac vein in the subject;
    reducing the observed stenosis or compression of the common iliac vein and increasing a cross-sectional area of a lumen of an obstructed or occluded portion of the common iliac vein of the subject by one or more of angioplasty, balloon angioplasty, and stenting of the iliac vein, and thereby reducing or eliminating the presence of hemorrhoids in the subject diagnosed with hemorrhoids;
    making one or more subsequent visual inspections of the lower rectum and anus after the step of reducing to determine the presence of hemorrhoids in the subject.

2. The method of claim 1, wherein the step of increasing the area of the lumen of the obstructed or occluded portion of the common iliac vein of the subject comprises implantation of a self-expanding stent or a balloon-expanded stent in the obstructed or occluded portion of the common iliac vein of the subject.

3. The method of claim 1, wherein the step of reducing stenosis or compression of the iliac vein comprises implantation of a self-expanding metallic stent or a balloon-expanded metallic stent in a stenosed or a compressed portion of the common iliac vein of the subject.

4. The method of claim 1, wherein the medical imaging is performed by a computed tomography pelvic scan system, a pelvic magnetic resonance imaging system, a computed tomography angiography system, a magnetic resonance angiography system, a computed tomographic venography system, a magnetic resonance venography system, a duplex scan venography system, an ultrasonography system, or an iliocavography system.

5. The method of claim 4, wherein the medical imaging system is a color Doppler ultrasonography system.

6. The method of claim 1, wherein the step of performing an intra-vascular visualization procedure is conducted using an Intra Vascular Ultrasound (IVUS) system or an optical coherence tomography angiography (OCT-A) system.

* * * * *